United States Patent [19]
Malouf

[11] Patent Number: 6,016,578
[45] Date of Patent: Jan. 25, 2000

[54] SURGICAL WASHBASIN

[76] Inventor: Hanna Malouf, 812, Rockland, Outremont, Canada, H2V 2Z9

[21] Appl. No.: 09/172,668

[22] Filed: Oct. 15, 1998

[51] Int. Cl.[7] ........................................................ A47K 1/04
[52] U.S. Cl. ................................... 4/619; 4/621; D23/284
[58] Field of Search ............................... 4/619, 621, 624, 4/519, 523; D23/284, 289, 288

[56] References Cited

U.S. PATENT DOCUMENTS

| D. 174,042 | 2/1955 | Kiefer | D23/284 |
| D. 332,828 | 1/1993 | Schaerrer | D23/284 |
| 758,447 | 8/1904 | Housholder | 4/523 |
| 1,361,887 | 12/1920 | Mattison | 4/519 |
| 1,848,385 | 3/1932 | Schindoski | |
| 1,898,314 | 2/1933 | Sandhagen | 4/519 |

Primary Examiner—David J. Walczak

[57] ABSTRACT

The front wall of this washbasin forms a central recess to receive the surgeon's waist while the bowl forms, on each side of the recess, a pocket which extends down to the bowl bottom. The surgeon's elbows are received within the pockets while the hands and forearms are being washed.

14 Claims, 2 Drawing Sheets

SURGICAL WASHBASIN

FIELD OF THE INVENTION

The present invention relates to washbasins and more particularly to a washbasin for use by surgeons for washing their hands and forearms prior to performing surgery.

BACKGROUND OF THE INVENTION

It is known that surgeons must spend a considerable time for completely washing their hands and forearms to disinfect the same before being presented with rubber gloves prior to performing surgery. Therefore, the washing must be effected in such a manner that the forearms always upwardly extend from the elbows to prevent washwater which might contain any type of germs from flowing back onto the hands.

Conventional washbasins are very awkward to use by surgeons for hand washing purposes since the elbows must be spread laterally to clear the upper edge of the washbasin.

U.S. Pat. No. 1,848,385 dated Mar. 8, 1932 to Ferdenand G. SCHINDOSKI and entitled "WASHBASIN" shows a washbasin which is characterized by a central front recess to permit the basin to extend rearwardly around the waist of the user but, here again, this washbasin is not suitable for use by surgeons since the top of the washbasin is co-extensive all around with the top edge of its bowl.

OBJECTS OF THE INVENTION

It is therefore the general object of the present invention to provide a washbasin particularly designed for use by surgeons for washing their hands and forearms prior to performing surgery.

Another object of the present invention is to provide a washbasin of the character described which specifically permits the surgeon to insert his elbows within the washbasin bowl with his forearms upwardly extending from the elbows while washing his hands to prevent washwater from flowing back onto the hands and also from dripping on the floor.

Another object of the present invention is to provide a washbasin of the character described which is manufactured as a unitary unit.

SUMMARY OF THE INVENTION

The washbasin of the invention is for use by surgeons and comprises a perimetral wall composed of generally straight back and side wall portions and of a front wall portion defining a central generally semi-circular recess and a lateral straight wall section on each side of said recess and generally parallel to said back wall portion, and a bottom wall merging with said perimetral wall whereby the bowl formed by said bottom and perimetral walls has two pockets, one on each side of said central recess, which extends down to said bottom wall. The central recess is of a size to receive a surgeon's waist and said front wall portion has a uniform height throughout.

Preferably, the back wall portion and adjacent sections of the side wall portions are higher than said front wall portion.

Preferably, said bottom wall has a drain opening and slopes down towards said opening.

Preferably, the top of said back wall portion is rearwardly extended by a flat and generally horizontal ledge and further including a splash board upstanding from the back of said ledge.

Preferably, said ledge has a central hole for the passage of a faucet water feeding pipe.

Preferably, said side and front wall portions have a top edge forming an inwardly downwardly sloping surface.

BRIEF DESCRIPTION OF THE DRAWINGS

In the annexed drawings, like reference characters indicate like elements throughout.

DETAILED DESCRIPTION OF THE PREFERRED EMBODIMENT

Figure 1:
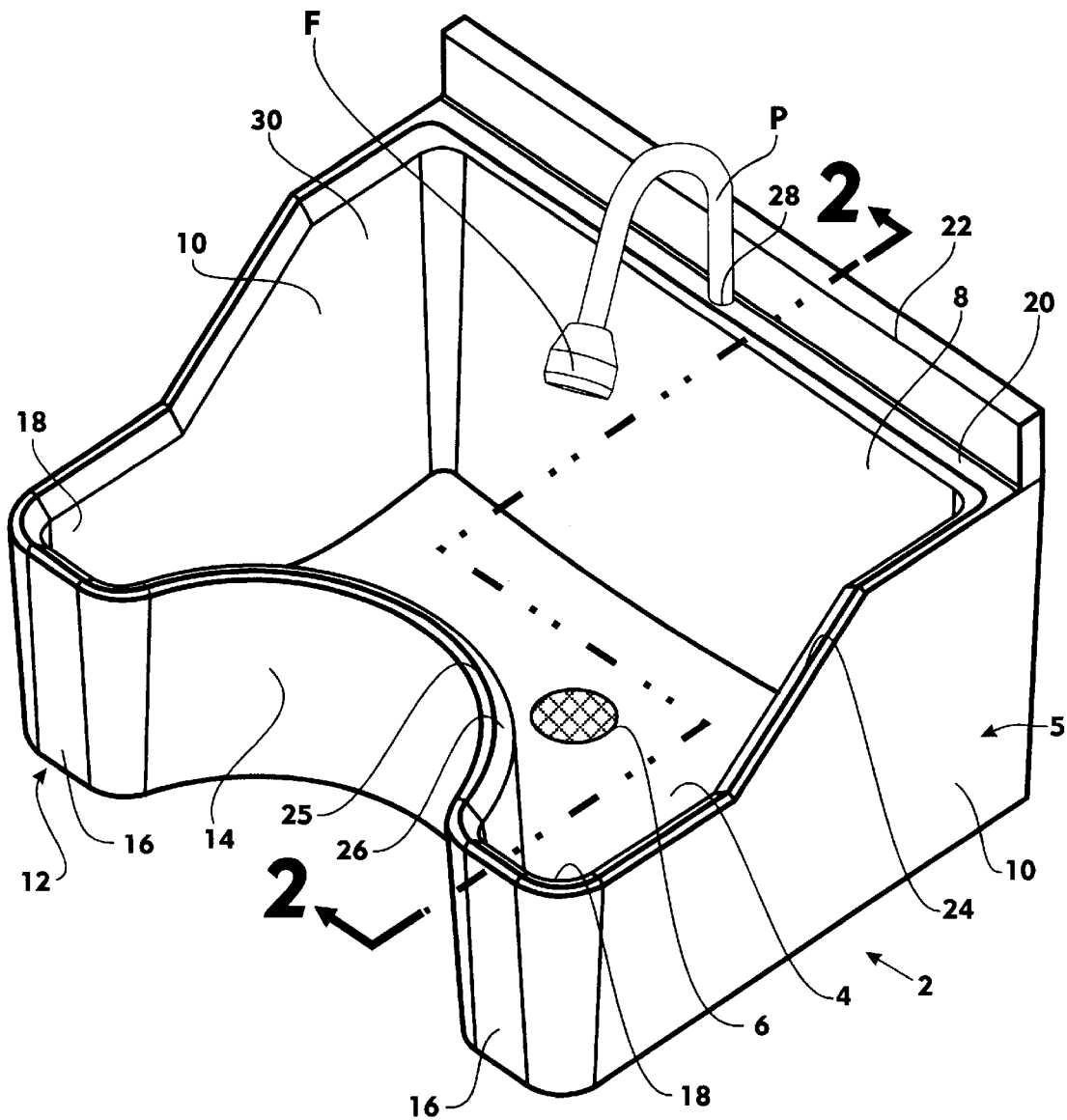
FIG. 1 is a perspective view of the washbasin of the present invention.
Figure 2:
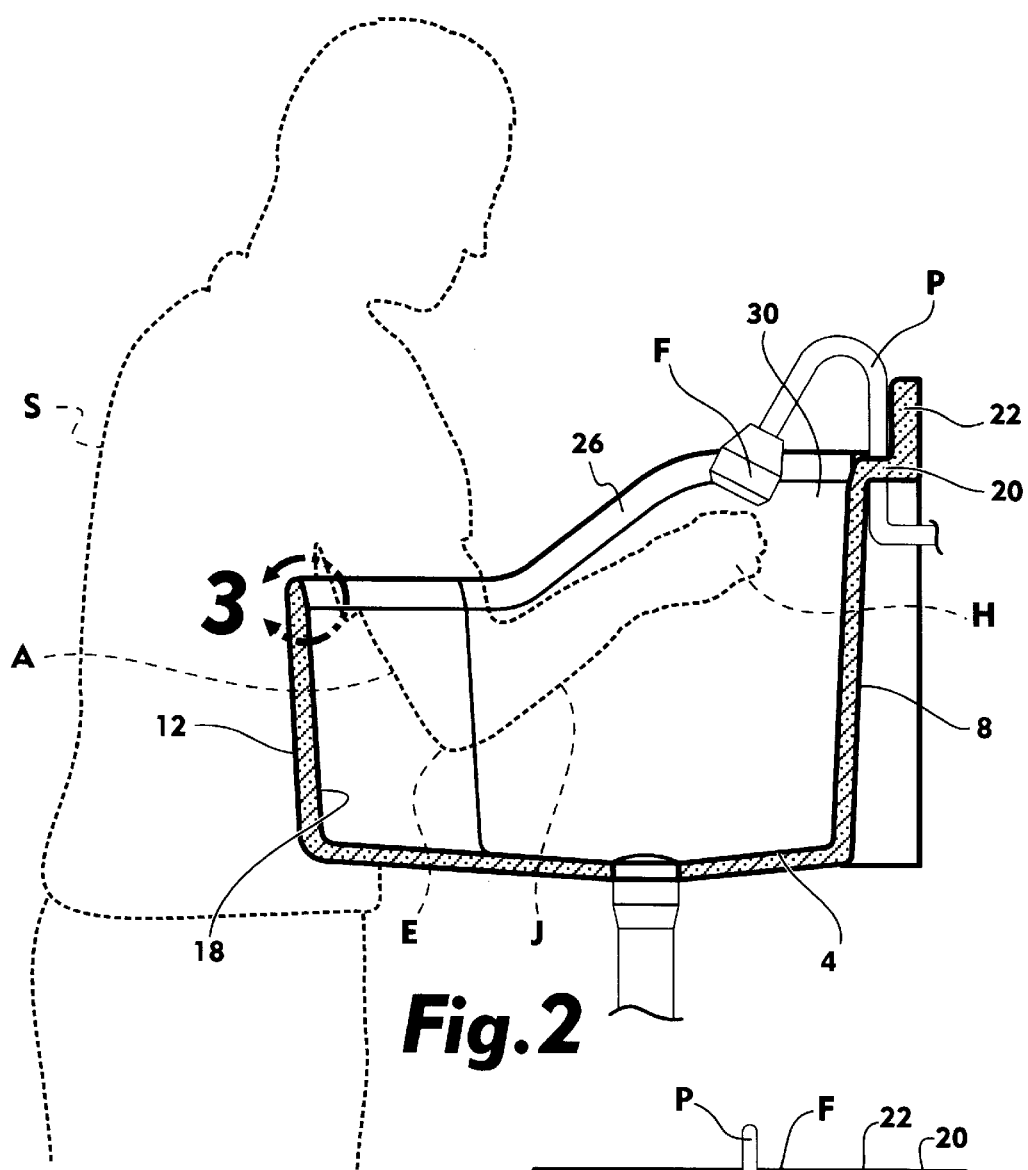
FIG. 2 is a vertical section taken along line 2—2 of FIG. 1.
Figure 3:
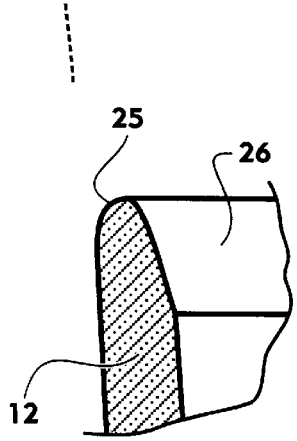
FIG. 3 is a partial section taken in area 3 of FIG. 2.
Figure 4:
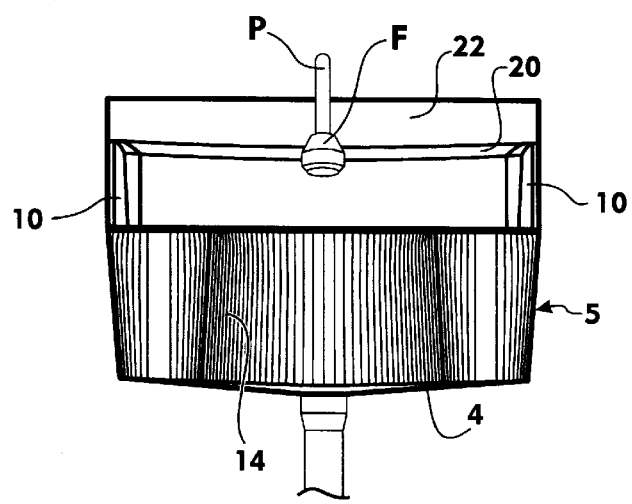
FIG. 4 is a front elevation of the washbasin.

Referring to FIGS. 1 to 4 the washbasin 2 of the present invention includes a bottom wall 4 and a perimetral wall 5 upstanding from and merging with the edges of bottom wall 4. The latter has a drain hole 6 at its center. The top surface of the bottom wall 4 slopes downwardly towards the drain hole 6. Perimetral wall 5 is defined a back wall 8, a pair of side walls 10 generally normal to the back wall 8 and a front wall 12 which forms a central semi-circular recess 14 with on each side thereof, a lateral straight wall section 16. Recess 14 is of a size to receive the surgeon's waist. Front wall 12 has a uniform height throughout, as shown in FIGS. 1, 2 and 4. The bowl formed by the bottom wall 4 and perimetral wall 5 defines pockets 18 on each side of the central recess 14 and these pockets extend all the way down to the bottom wall 4.

A ledge 20 rearwardly extends from the top of the back wall 8 and a splashboard 22 upwardly extends from the rear of ledge 20. The top ledge 20 is slightly downwardly slanted from both sides towards its center to allow flowing of any spilled over washwater down the washbasin 2.

The top edges 24 and 25 of the side walls 10 and front wall 12 respectively, define an inner downwardly slanting surface 26 to prevent washwater from falling onto the floor.

A hole 28 is made through the center of top ledge 20 for receiving the pipe P of a faucet F. The faucet F is positioned at a lower level than ledge 20 and top edge 24 of the back section 30 of each side wall 10. Front wall 12 is lower than back wall 8.

As clearly shown in FIG. 2, a surgeon S can wash his hands under the faucet F while his elbows E are conveniently positioned within the pockets 18 with the arm's portion from shoulder to elbows downwardly extending close to the surgeon's waist and with his forearms J upwardly extending towards the faucet F. Therefore, washwater falling on the hands flows downwardly towards the elbows and drops within the bowl of washbasin 2; it cannot reverse direction towards the hands and therefore eliminating the possibility of recontaminating the washed hands with germs.

It has been found that effective hands and forearms washing can be carried out in this manner.

In a preferred embodiment, the washbasin of the present invention preferably has the following dimensions:

its overall width is 80 cm;

its overall depth is 68 cm;

the semi-circular recess has a radius of 20 cm;

the width of the ledge is 5 cm;

the thickness of the splashboard is 3 cm;

the thickness of the perimetral wall is about 3 cm;

the height from the top surface of the bottom wall to the top of the front wall is 28 cm and to the top ledge is 42 cm;

the splashboard has a height of about 8 cm.

I claim:

1. A washbasin for use by surgeons comprising a perimetral wall composed of generally straight back and side wall portions and of a front wall portion defining a central generally semi-circular recess of a size to receive the surgeon's waist and a lateral straight wall section on each side of said recess and generally parallel to said back wall portion, and a bottom wall merging with said perimetral wall whereby the bowl formed by said bottom and perimetral walls has two pockets, one on each side of said central recess, which extends down to said bottom wall said front wall portion having a uniform height throughout.

2. A washbasin as defined in claim 1, wherein said back wall portion and adjacent sections of said side wall portions are higher than said front wall portion.

3. A washbasin as defined in claim 2, wherein said side and front wall portions have a top edge forming an inwardly downwardly sloping surface.

4. A washbasin as defined in claim 2, wherein said bottom wall has a drain opening and slopes down towards said opening.

5. A washbasin as defined in claim 4, wherein said side and front wall portions have a top edge forming an inwardly downwardly sloping surface.

6. A washbasin as defined in claim 2, wherein the top of said back wall portion is rearwardly extended by a flat and generally horizontal ledge and further including a splash board upstanding from the back of said ledge.

7. A washbasin as defined in claim 6, wherein said side and front wall portions have a top edge forming an inwardly downwardly sloping surface.

8. A washbasin as defined in claim 6, wherein said ledge has a central hole for the passage of a faucet water feeding pipe.

9. A washbasin as defined in claim 8, wherein said bottom wall has a drain opening and slopes down toward said opening.

10. A washbasin as defined in claim 9, wherein said side and front wall portions have a top edge forming an inwardly downwardly sloping surface.

11. A washbasin as defined in claim 8, wherein said side and front portions have a top edge forming an inwardly downwardly sloping surface.

12. A washbasin as defined in claim 6, wherein said bottom wall has a drain opening and slopes down toward said opening.

13. A washbasin as defined in claim 12, wherein said side and front wall portions have a top edge forming an inwardly downwardly sloping surface.

14. A washbasin as defined in claim 1, wherein said side and front wall portions have a top edge forming an inwardly downwardly sloping surface.

* * * * *